(12) United States Patent
Leiner et al.

(10) Patent No.: US 7,677,417 B2
(45) Date of Patent: Mar. 16, 2010

(54) STORAGE/DISPENSING SYSTEM AND METHOD FOR THE APPLICATION OF A FLOWABLE SUBSTANCE

(75) Inventors: Uwe Leiner, Midlum (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 720 days.

(21) Appl. No.: 10/941,596

(22) Filed: Sep. 14, 2004

(65) Prior Publication Data

US 2006/0037972 A1 Feb. 23, 2006

(30) Foreign Application Priority Data

Aug. 18, 2004 (DE) .................... 10 2004 040 099

(51) Int. Cl.
*B65D 37/00* (2006.01)
(52) U.S. Cl. ............... 222/212; 222/1; 222/108; 222/111; 222/213; 222/546; 222/562; 222/563; 222/567
(58) Field of Classification Search ......... 222/212–215, 222/420–421, 544, 569, 566–567, 562, 1, 222/108, 111, 546, 563, 554
See application file for complete search history.

(56) References Cited

U.S. PATENT DOCUMENTS

| | | | | |
|---|---|---|---|---|
| 2,436,291 A | * | 2/1948 | Daniel | 15/257.05 |
| 2,673,661 A | * | 3/1954 | Barton | 222/212 |
| 2,987,223 A | * | 6/1961 | Armour | 222/207 |
| 3,240,405 A | * | 3/1966 | Abbott | 222/543 |
| 4,498,609 A | * | 2/1985 | Stock | 222/420 |
| 5,129,825 A | * | 7/1992 | Discko, Jr. | 433/90 |
| 5,263,615 A | * | 11/1993 | Anderson et al. | 222/212 |
| 5,373,964 A | * | 12/1994 | Moore | 222/1 |
| 5,975,381 A | * | 11/1999 | Revenu | 222/563 |
| 6,076,709 A | * | 6/2000 | Wilner | 222/212 |
| 6,616,019 B2 | * | 9/2003 | D'Alessio et al. | 222/566 |
| 7,213,727 B2 | * | 5/2007 | Kokubo | 222/212 |
| 7,308,988 B2 | * | 12/2007 | Yashima et al. | 215/344 |
| 2001/0050293 A1 | * | 12/2001 | Phinn | 222/566 |
| 2005/0211734 A1 | * | 9/2005 | Spada et al. | 222/420 |

* cited by examiner

*Primary Examiner*—Frederick C. Nicolas
(74) *Attorney, Agent, or Firm*—Novak Druce+Quigg; Gregory A. Nelson; Gregory M. Lefkowitz

(57) ABSTRACT

A storage/dispensing system (9) for a flowable dental substance is described with a solvent-tight, resiliently deformable container (10) for the storage and provision of the flowable dental substance and a dispensing device (1) connected to the container (10) for discharging the flowable dental substance from the container (10), with a cup (2) which has an outlet orifice (3) and a wall (4, 4') in which a passage orifice (5) is provided for introducing the flowable dental substance from the container (10), wherein the passage orifice (5) has a cross-sectional area of 0.001 to 0.1 mm$^2$ and the outlet orifice (3) has a cross-sectional area of 0.5 to 5 mm$^2$, and wherein the inside of the cup (2) has a cross-section which is constant and/or reduces from the passage orifice (5) to the outlet orifice (3).

23 Claims, 3 Drawing Sheets

STORAGE/DISPENSING SYSTEM AND METHOD FOR THE APPLICATION OF A FLOWABLE SUBSTANCE

BACKGROUND OF THE INVENTION

1. Field of the Invention

The invention relates to a storage/dispensing system for a flowable dental substance, in particular for storing and dispensing small quantities of dental substances with an elevated content of highly volatile solvents, such as flowable dental adhesives, fluoride varnishes, liners or desensitisers. The invention furthermore relates to a storage/dispensing/application system for a flowable dental substance and to a dental system and to a method for the application of a flowable dental substance.

2. Description of the Related Art

In dentistry, dental adhesive materials, varnishes or desensitisers are often formulated on the basis of organic solvents such as for example acetone, ethyl acetate, ethanol or propanol. The organic solvents sometimes also act as diluents and/or suspending agents. The organic solvents exhibit an elevated vapour pressure. Containers which are capable of providing stable storage for these solvents over an extended period are generally made from solvent-tight films which comprise at least one diffusion-proof barrier layer, such that gas diffusion, in particular of organic solvents such as acetone, ethyl acetate, ethanol and propanol, is suppressed and the composition of the flowable dental substance undergoes no change. An aluminium laminate film is generally used as the barrier layer which, due to the effective barrier action of the metallic layer, ensures that there is no diffusion loss of liquid constituents. The laminate film additionally provides protection from light for any photosensitive substances possibly present in the dental material (the flowable dental substance).

Various systems for the storage and metered application of small quantities of dental materials are known. EP 0 895 943, WO 98/23220, EP 0 770 021, DE 31 22 237 and DE 298 14 215, for example, disclose various "single-dose" devices, some of which may contain small quantities of dental material and comprise an integral application tool on a storage vessel in such a manner that, for example, when the tool is simply pressed into the container, the tool is wetted with the predosed dental material which is to be applied, so permitting straightforward single use. Storage and application devices are furthermore known in which the device itself comprises no integral application tool, for example from EP 1 153 579. The stated devices are both simple to operate and hygienic to use, but are disposable articles. Multiple-use articles which may be used repeatedly are more resource-efficient, in particular with regard to packaging materials, which is desirable in times of increased environmental awareness.

In the dental materials sector, DE 197 13 951 discloses a container/dropper system for dental adhesive which serves as a multiple-use container for the storage and application of a dental adhesive which is dissolved in acetone or ethyl acetate and is polymerisable with visible light. DE 197 13 951 proposes a resiliently deformable plastics bottle with a dropper insert which is rendered diffusion-proof with regard to volatile solvents by using laminate layers and which is capable of supplying a controlled quantity of the dental material. Colouring of the bottle wall additionally makes the container opaque to visible light. One possible structure of the container wall is known, for example, from WO 98/31742. With the aim of controlling the dropping speed of low viscosity liquids, DE 197 13 951 proposes using a dropper insert with a dropper channel which widens from the inside outwards, wherein the diameter at the discharge end corresponds to the desired drop size and the diameter at the inlet end is within a range between 0.1 and 0.25 mm and determines the flow rate of the dental material. It is to be assumed that the design principle underlying this bottle and the configuration of the dropper channel is that pressure builds up within the bottle after resilient deformation thereof, which pressure drives the liquid through the small opening at the inlet end into the dropper channel. Due to the widening channel, the volume available for the upwardly moving liquid increases, the liquid then being under virtually no pressure. When the bottle is upended, gravity enables the liquid to overcome the capillary forces and surface tension which are retaining it in the dropper channel and the liquid leaves the channel dropwise.

A dropper channel whose diameter is greater at the inlet end than the diameter at the discharge end is also disclosed in EP 0 431 885, U.S. Pat. No. 5,221,017 and U.S. Pat. No. 6,129,248.

When applying a dental material, a dentist is generally anxious to ensure that the dental material is applied onto the patient's tooth as quickly as possible using an application instrument, for example a microbrush. If the dropper channel is of a shape which widens from the inside outwards, as in the known devices just described above, the head of a microbrush which is introduced into the channel will seal it so effectively that discharge of the material is no longer possible. Furthermore, the insertion of a brush head into the channel may deform the channel in such a manner that dispensing characteristics are modified. There is furthermore a risk that when the brush is inserted into the channel, the bristles located on the side of the brush will bend, which would impair the proper functioning of the brush.

Another configuration of the dropper channel, namely a dropper channel which tapers in towards the discharge end, is known from U.S. Pat. No. 6,223,947. However, direct discharge of the dental material onto an application instrument proves difficult in this case.

SUMMARY OF THE INVENTION

The primary object of the invention is to provide a device for storing and dispensing small quantities of a flowable substance, in particular of a polymerisable dental material with an elevated content of organic, highly volatile solvents, which device may be used repeatedly, permits simple dispensing and ensures direct discharge of the dental material onto an application instrument. Further objects of the present invention are to provide a corresponding storage/dispensing system, a corresponding storage/dispensing/application system, a corresponding dental system and a method for the application of a flowable substance.

The primary object is achieved by a storage/dispensing system for a flowable dental substance with a solvent-tight, resiliently deformable container for the storage and provision of the flowable dental substance and a dispensing device connected to the container for discharging the flowable dental substance from the container, with a cup which has an outlet orifice and a wall in which a passage orifice is provided for introducing the flowable dental substance from the container, wherein the passage orifice has a cross-sectional area of 0.001 to 0.1 mm$^2$ and the outlet orifice has a cross-sectional area of 0.5 to 5 mm$^2$, and wherein the inside of the cup has a cross-section which is constant and/or reduces from the passage orifice to the outlet orifice.

The invention is based on the finding that a cup with an appropriately small cross-section is, on the one hand, suitable for accommodating small quantities of a (particularly dental, c.f. above) flowable substance from the container in which the flowable substance may be securely and durably stored and, on the other, is suitable for allowing the flowable substance to be picked up purposefully by an application instrument. It is additionally possible when the cup is present to dispense the flowable substance dropwise in a specified form with the dispensing device. The small cross-sectional area of the passage orifice ensures that the feed stream of flowable substance into the cup is small enough to permit controlled dispensing. The size of the passage orifice determines the speed of introduction of a flowable substance into the cup, such that it is possible to introduce flowable substance from the container into the cup in a controlled manner. The shape of the cup (as defined above by the dimension of the discharge area and the stated cross-sectional area within the cup) makes it possible purposefully to introduce an application instrument and to pick up flowable substance with said application instrument from within the cup. The cup forms a step on which the flowable substance can collect and from which it may be picked up by an application instrument. If the inside of the cup widens out from the outlet orifice in the direction of the passage orifice, the cup can accommodate a larger quantity of the flowable substance without this having any effect on the size of a drop which forms at the outlet orifice as the corresponding drop size is substantially determined only by the circumference of the outlet orifice and the surface tension of the flowable substance. It has surprisingly been found that well controlled dispensing is possible without the flowable substance being sprayed in a jet out of the passage orifice. Since the container is designed to be resiliently deformable, it is possible by compressing the container to exert pressure on a flowable substance located within the container in order to drive the substance through the passage orifice.

In a development of the invention, on the opposite side of the passage orifice to the cup there is a passage channel, wherein the passage channel has a cross-section which is constant and/or decreases towards the passage orifice. The passage channel is intended to assist the introduction of the flowable substance through the passage orifice.

In a preferred development of the invention, the inside of the cup has a volume of 1 to 30 $mm^3$. Preferred dispensed quantities or quantities picked up by an application instrument are within the stated range.

In another development, a circumferential collecting groove is provided on the outside of the dispensing device for collecting any flowable substance which escapes from the container. If escaping flowable substance is collected in the collecting groove, this prevents any other external surfaces of the dispensing device from becoming contaminated by the flowable substance.

In a further development of the invention, the container and the dispensing device are connected together in leak-proof manner relative to the flowable substance (such that said substance or the constituents thereof cannot escape at the connection points), wherein the dispensing device has first catch means and the container second catch means to secure the connection, wherein the catch means correspond to one another. The mutually associated catch means ensure that the connection between the container and dispensing device remains leak-proof with regard to unwanted escape of the flowable substance or constituents of the flowable substance even when in service.

In a preferred development of the invention the container has an internal volume of 1 to 20 ml. This volume allows the container to accommodate a sufficient quantity of the flowable substance and makes it easy to handle. In individual cases, a larger capacity of the container may, however, be convenient depending on the volume of individual dispensed amounts.

In a further development of the invention, the storage/dispensing system is opaque to at least a proportion of visible light, in particular to blue light. Keeping at least a proportion of visible light out enables the storage/dispensing system also to store and dispense flowable dental substances which, for example, cure on exposure to light, for instance blue light. The person skilled in the art may find possible configurations for the container wall and for opacity, for example, in DE 197 13 951.

A further object of the invention is achieved by a storage/dispensing/application system for a flowable dental substance which system comprises a storage/dispensing system as described above and an application instrument, in particular a microbrush, wherein the application instrument is constructed in such a manner that at least a pick-up portion thereof may be inserted through the outlet orifice into the cup in order to pick up flowable dental substance therein. Although a flowable dental substance may be applied simply by dropping, application may be metered and controlled more precisely by means of an application instrument. Adaptation of the application instrument and the cup to one another enables simple and reliable pick-up of flowable dental substance by the application instrument. Removing the flowable dental substance from the cup by means of the application instrument ensures that, despite the elevated fluidity of the flowable dental substance, the flowable dental substance does not soil the outside of the storage/dispensing system, unlike when the flowable substance is discharged dropwise from a conventional dispensing device.

A further object of the invention is achieved by a dental system which comprises a storage/dispensing/application system as described above or a storage/dispensing system as described above, wherein a flowable dental substance is provided in the container and may be introduced into the cup via the passage orifice of the dispensing device.

With regard to the method, the object is achieved by a method for the application of a flowable dental substance comprising the following steps:

provision of a dental system according to the invention,
introduction of flowable dental substance into the cup from the container through the passage orifice,
removal of the flowable dental substance from the cup by means of the application instrument,
application of the flowable dental substance by means of the application instrument.

Thanks to the cup, the application instrument may purposefully be guided to the flowable dental substance to be removed, which substance is introduced into the cup, such that a precise, metered quantity of the flowable dental substance may be applied by means of the application instrument. It is preferred firstly to insert the application instrument, for example a microbrush, into the cup and then to upend the storage/dispensing system in order to allow the quantity of flowable dental substance, which has been dispensed in the form of a drop, to run down into the application instrument. A drop in the cup could otherwise inadvertently fall out.

BRIEF DESCRIPTION OF THE DRAWINGS

The invention is illustrated in greater detail below by means of advantageous embodiments with reference to the attached Figures, in which.

DETAILED DESCRIPTION OF THE INVENTION

Figure 1A:
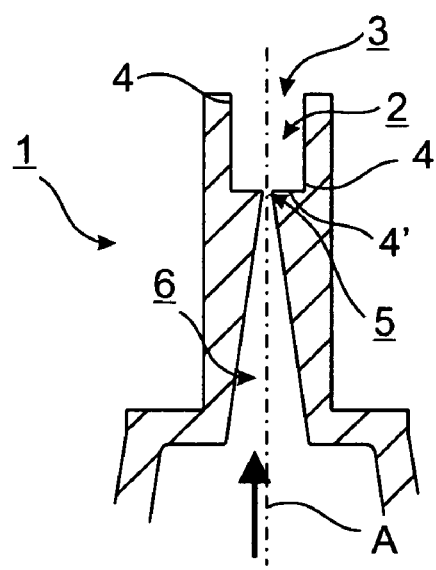
FIGS. 1a and 1b show a schematic sectional view of a first embodiment of a dispensing device according to the invention.

FIG. 1a shows a schematic sectional view of a first embodiment of a dispensing device 1 according to the invention. The dispensing device 1 shown here is rotationally symmetrical around an axis A. The dispensing device 1 has a cup 2, which has an outlet orifice 3 and a circumferential wall 4. In the embodiment shown here, a passage orifice 5 is provided in the wall zone 4' opposite to the outlet orifice 3, into which a (in the drawing upwardly) tapering passage channel 6 opens. The cup 2 corresponds to a cylinder, wherein one end face of the cylinder is formed by the outlet orifice 3 and the other end face by the wall 4' with the passage orifice 5. A flowable substance may be introduced into the passage channel 6 in the direction indicated by the arrow and reaches the passage orifice 5, the cross-sectional area of which determines the flow rate (volume per unit time) at which the flowable substance can pass into the inside of the cup 2.

Figure 1B:
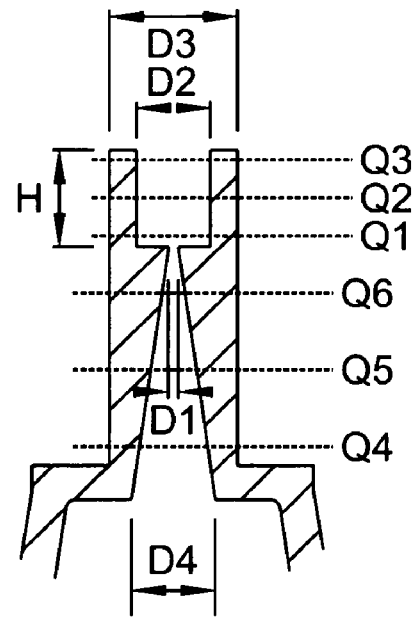

The dispensing device 1 shown in FIG. 1a is also shown in FIG. 1b. For clarity's sake, the reference numerals from FIG. 1. are not repeated, but cross-sectional planes and dimensions are instead drawn in. In the embodiment shown here, the inside of the cup 2 is of constant cross-sectional area in the planes Q1, Q2, Q3, which are perpendicular to the plane of the drawing. The outlet orifice 3 has a cross-sectional area of 0.5 to 5 $mm^2$ and preferably corresponds to a circular area with a diameter D2 of 1 to 2 mm, particularly preferably with a diameter D2 of 1.5 mm.

In an alternative which is not shown, the cross-sectional areas of the inside of the cup may increase in size from the outlet orifice to the passage orifice. For example, the cross-sectional area at plane Q3 may be smaller than the cross-sectional area at plane Q2, which may in turn be smaller than the cross-sectional area at plane Q1.

The passage orifice 5 has a cross-sectional area of 0.001 to 0.1 $mm^2$; it is preferably a circular area with a diameter D1 of 0.05 to 0.25 mm, particularly preferably with a diameter D1 of 0.15 mm. In the embodiment shown according to FIGS. 1a and b, the cup 2 has a height H of 2.5 mm. The tip of the dispensing device 1 has an external diameter D3 of 2.6 mm. The diameter of the passage channel 6 corresponds at one end to the diameter D1 of the passage orifice 5. At the opposite end, the passage channel 6 preferably has a diameter D4 of 1 to 4 mm. A diameter D4 of 1.7 mm is particularly preferred.

In the preferred embodiment shown in FIGS. 1a and b, the cross-sectional areas decrease in size, i.e. the cross-sectional area of the passage channel 6 at the plane Q4 is greater than the cross-sectional area at the plane Q5, which is in turn greater than the cross-sectional area at the plane Q6. The passage channel 6 may alternatively comprise portions of constant cross-sectional area up to the passage orifice 5.

Figure 2:
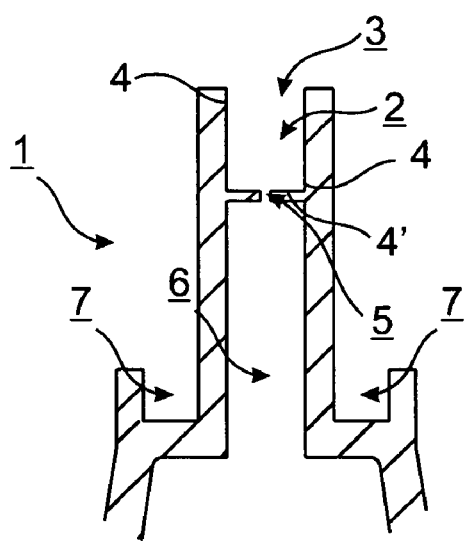
FIG. 2 shows a schematic sectional view of a second embodiment of a dispensing device according to the invention.

FIG. 2 shows another embodiment of a dispensing device 1 according to the invention. The cup 2 is configured in the same manner as the embodiment shown in FIGS. 1a and 1b. In the embodiment shown in FIG. 2, the passage channel 6 is of constant cross-sectional area, such that the passage channel 6 corresponds to a cylinder, one end face of which contains the passage orifice 5. Furthermore, a circumferential collecting groove 7 is provided on the outside of the dispensing device 1 for collecting any flowable substance which escapes from the cup 2. The flowable substance, which escapes from the cup 2 through the outlet orifice 3 and runs down the outside of the dispensing device 1, may be collected in the collecting groove 7, and is accordingly prevented from soiling the rest of the dispensing device.

The preferred embodiments illustrated in FIGS. 1a, b and 2 are rotationally symmetrical and the cup 2, the outlet orifice 3, the passage orifice 5 and the passage channel 6 are coaxial. However, the subject matter of the invention is not restricted to these embodiments, especially since the cup, the outlet orifice, the passage orifice and the passage channel may assume other shapes, for example an oval, slot-like or polygonal shape. Furthermore, the centre axes may be offset relative to one another. The passage orifice 5 and outlet orifice 3 of the cup 2 may furthermore be so arranged that they are not opposite one another, for example the passage orifice 5 may even be provided in a side wall of the cup 2, such that the planes of the passage orifice 5 and the outlet orifice 2 are at an angle, for example a right angle, to one another.

Figures 3A, 3B:
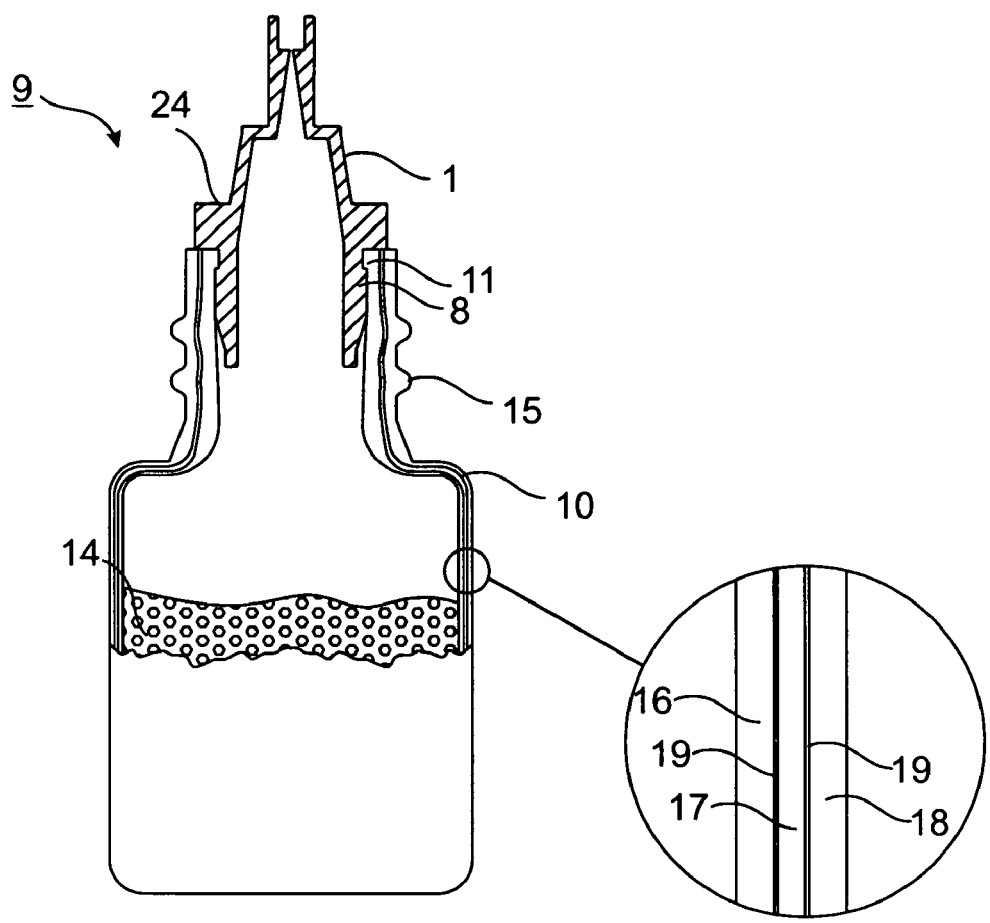
FIG. 3a shows a schematic, partially sectional view of an embodiment of a storage/dispensing system according to the invention.
FIG. 3b shows a magnified sectional view of a side wall of the storage/dispensing system from FIG. 3a, FIG. 4 shows a view of a closure cap for the storage/dispensing system from FIG. 3a, FIG. 5 shows a schematic view of the embodiment shown in FIG. 3a of a storage/dispensing system according to the invention with a screwed on closure cap

FIG. 3a shows a schematic section through an embodiment of a storage/dispensing system 9 according to the invention. The storage/dispensing system 9 comprises a container 10 and a dispensing device 1. The dispensing device 1 was described above with reference to FIGS. 1a, 1b and 2. The container 10 illustrated takes the form of a bottle and the dispensing device 1 has been inserted into the neck of the bottle, such that the cup 2 is connected with the inside of the bottle via the passage orifice 5 and the passage channel 6. The bottle neck of the container 10 has an external thread 15. The dispensing device comprises an abutment surface 24, whose function will be described below. The dispensing device 1 has been inserted into the bottle neck and comprises, in the zone insertable into the container 10, a skirt 8 which is slightly larger in diameter than the orifice of the container 10, so providing a leak-proof press fit when assembled. The container 10 has an undercut 11 in its inner, upper neck zone, which undercut, together with the skirt 8, constitutes catch means which form a snap action mechanism ensuring that the dispensing device 1 is held securely inside the container 10 even under considerable internal pressure. In the case of a deformable container 10, an elevated internal pressure may be generated by compression of the container 10 and serves to force flowable substance out of the container 10 through the passage channel 6 and the passage orifice 5 into the cup 2. The container 10 serves to store and provide a flowable substance 14, which may be introduced through the bottle neck of the container 10, the passage channel 6 and the passage orifice 5 into the inside of the cup 2 of the dispensing device 1.

The container and the dispensing device may, according to an alternative embodiment not illustrated in the drawings, form a single-component storage/dispensing system, which may then comprise a further closable orifice for filling the storage/dispensing system with a flowable substance.

The container 10 may be of resilient construction at least in places, such that it is possible to build up an elevated pressure inside the container 10 by compressing the container 10.

The wall of the container 10 consists of an inner layer 16, a barrier layer 17 and an outer layer 18, which are held stably together by means of coupling agent layers 19, as shown in FIG. 3b. The inner layer 16 and outer layer 18 may consist of polyolefins such as polyethylene, polypropylene, polybutylene, polystyrene, polycarbonate or hydrocarbon polymers of similar structure. Polyethylene is preferred. Barrier layer materials which may preferably be considered are polyamides, polyepoxides, polyesters, polyvinyl alcohols or mixtures and copolymers thereof. Polyvinyl alcohols are preferred.

Coupling agent 19 may, as illustrated, either be applied separately between the layers 16, 17, 18 (5 layer structure) or take effect by direct addition to the layers 16, 18, for example of polyolefin, and/or the barrier layer 17 (3 layer structure, not illustrated). A further alternative is a 2 layer structure (not illustrated), in which a barrier layer inside and, for example, a polyolefin layer on the outside form the wall of the container.

The container 10 has an internal volume of 1 to 20 ml, preferably of 3 to 15 ml.

Figure 4:
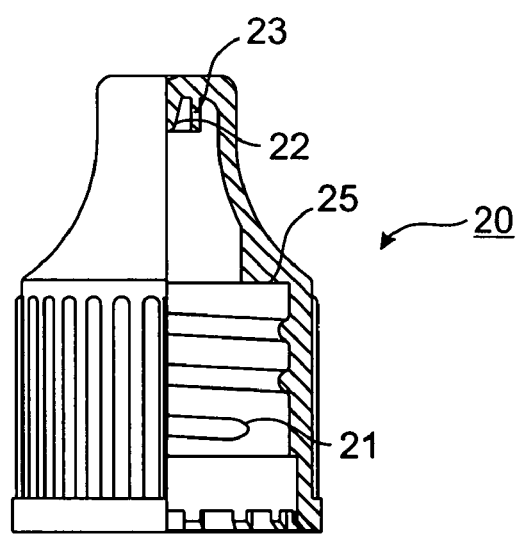

FIG. 4 shows a view of a closure cap 20, for the storage/dispensing system 9, as shown in FIG. 3a. The closure cap 20 comprises an internal thread 21, which corresponds to the external thread 15. Furthermore, the closure cap 20 comprises a protrusion 22 which, when the cap is screwed on, projects into the cup 2 of the dispensing device 1. A ring 23 is additionally provided. The inside of closure cap 20 has an abutment surface 25, which corresponds to an abutment surface 24 of the dispensing device 1, as explained below with reference to FIG. 5.

Figure 5:
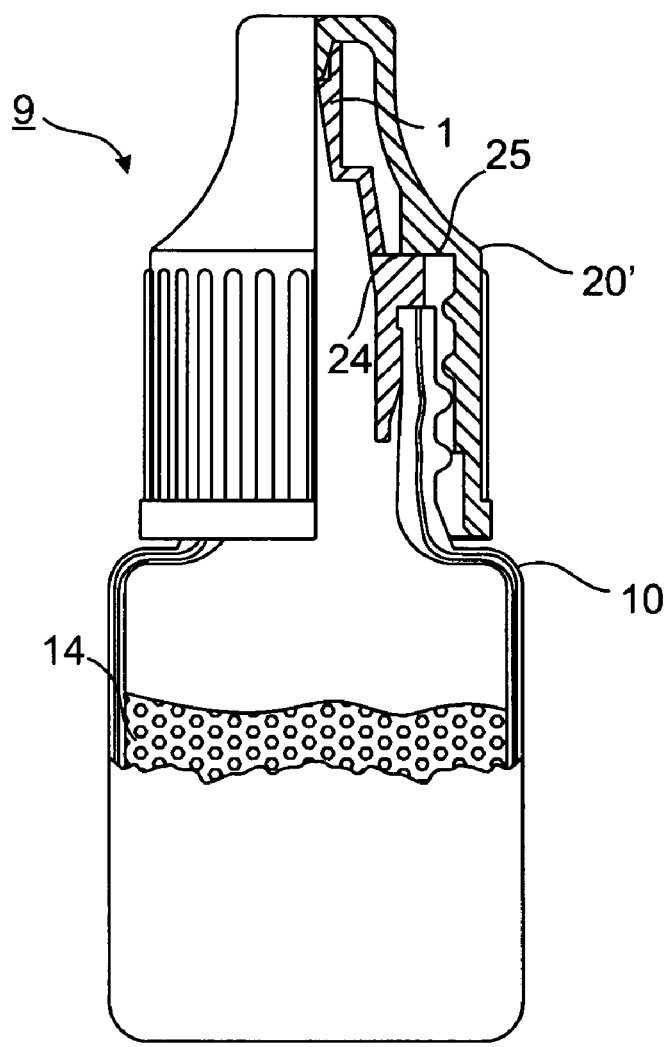

FIG. 5 shows a storage/dispensing system 9 with a screwed-on closure cap 20' (like closure cap 20 but without ring 23). When the cap is screwed on, the external thread 15 of the container 10 and the internal thread 21 of the closure cap 20 engage in one another. The abutment surfaces 24 and 25 limit the depth to which the closure cap 20 can be screwed down by coming into contact with one another. In this manner, the inside of the storage/dispensing system 9 is additionally sealed. The protrusion 22 is dimensioned such that, when the cap is maximally screwed down, the protrusion rests firmly at least against the wall 4 of the cup 2 opposite to the outlet orifice 3. This effects additional improvement of the sealing action. Further improvement may be achieved by using a ring 23, which rests against the side wall 4 of the cup 2, c.f. FIG. 4.

Figure 6:
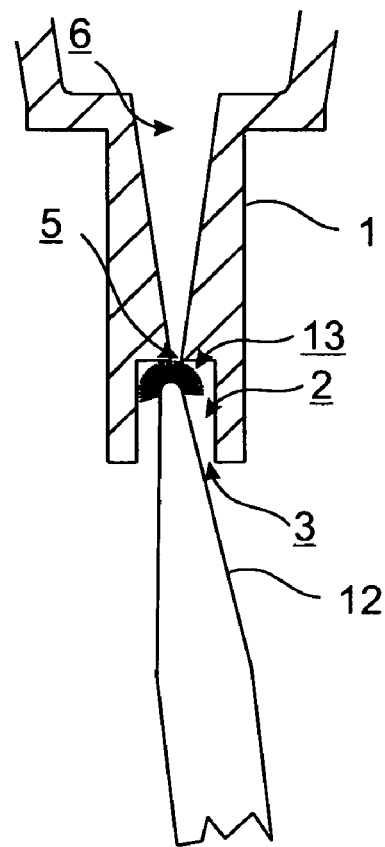
FIG. 6 shows a schematic view of the dispensing device from FIGS. 1a and 1b with an application instrument.

FIG. 6 shows an embodiment of the dispensing device 1 according to the invention with an application instrument 12. The dimensions of a pick-up portion of the application instrument 12 and the cup 2 of the dispensing device 1 are adapted to one another in such a manner that the pick-up portion 13 may be inserted through the outlet orifice 3 into the cup 2 in order to pick up flowable substance therein. Flowable substance may, for example, be picked up by tipping or upending a storage/dispensing system filled with a flowable substance such that the flowable substance passes through the passage channel 6 to the passage orifice 5. If the container 10 is, for example, of resilient construction, pressure may be exerted on the flowable substance by compression of the container 10, which pressure drives the flowable substance through the passage orifice 5 into the inside of the cup 2, where the flowable substance may be picked up by the pick-up portion 13 of the application instrument 12.

A dispensing device according to the invention may be used repeatedly and, together with a container, may constitute a repeatedly usable storage/dispensing system for a flowable substance, with which the flowable substance may be securely stored, accurately dispensed and optionally applied. Application of the flowable substance is simplified by the use of an application instrument. The method according to the invention for the application of a flowable substance permits simple and repeated application without limitations with regard to accuracy and without any risk of damage to the dental system used.

The invention claimed is:

1. A storage/dispensing system (9) for a flowable dental substance, comprising
   a solvent-tight, resiliently deformable container (10) for the storage and provision of the flowable dental substance, and
   a dispensing device (1) connected to the container (10) for discharging the flowable dental substance from the container (10), the dispensing device having
      a cup (2) which has an outlet orifice (3) and a wall (4, 4') in which a passage orifice (5) is provided for introducing the flowable dental substance from the container (10), and
      a passage channel (6) on the opposite side of the passage orifice (5) to the cup (2), the passage channel (6) having a cross-section which is constant or decreases towards the passage orifice (5) in a discharging direction of the flowable dental substance, and
   a closure cap (20) having a ring (23) resting against an outside wall of a side wall (4) of the cup (2) wherein a space exists between the ring (23) and an inner wall surface of the closure cap (20) when the closure cap (20) is attached to the dispensing device (1), wherein an entire exterior of said sidewall (4) of the cup (2) is in parallel alignment with an interior surface of said ring (23) and wherein said closure cap further comprises a protrusion that rests firmly against a bottom of said cup when said closure cap is attached to the dispensing device.

2. The storage/dispensing system (9) according to claim 1, wherein the inside of the cup (2) has a volume of about 1 to about 30 mm$^3$.

3. The storage/dispensing system (9) according to claim 1, wherein a circumferential collecting groove (7) is provided on the outside of the dispensing device (1) for collecting any flowable substance which escapes from the cup (2).

4. The storage/dispensing system (9) according to claim 1, wherein the container (10) has an internal volume of about 1 to about 20 ml.

5. The storage/dispensing system (9) according to claim 1, wherein the storage/dispensing system (9) is opaque to at least a proportion of visible light.

6. The storage/dispensing system (9) according to claim 5, wherein the storage/dispensing system (9) is opaque to at least a proportion of blue light.

7. The storage/dispensing system according to claim 1, wherein the passage orifice (5) has a cross-sectional area of about 0.001 to about 0.1 mm$^2$ and the outlet orifice (3) has a cross-sectional area of about 0.5 to about 5 mm$^2$.

8. The storage/dispensing system (9) according to claim 1, wherein the inside of the cup (2) has a cross-section which is constant or reduces from the passage orifice (5) to the outlet orifice (3).

9. The storage/dispensing system (9) according to claim 1, wherein the container (10) and the dispensing device (1) are connected together in leak-proof manner relative to the flowable dental substance and constituents thereof, wherein the dispensing device (1) has first catch means (8) and the container has second catch means (11) to secure a connection of the container (10) and the dispensing device (1), wherein the catch means (8, 11) correspond to one another.

10. A storage/dispensing/application system for a flowable dental substance, comprising
  a storage/dispensing system (9) for flowable dental substance, including
    a solvent-tight, resiliently deformable container (10) for the storage and provision of the flowable dental substance, and
    a dispensing device (1) connected to the container (10) for discharging the flowable dental substance from the container (10), the dispensing device having
      a cup (2) which has an outlet orifice (3) and a wall (4, 4') in which a passage orifice (5) is provided for introducing the flowable dental substance from the container (10), and
      a passage channel (6) on the opposite side of the passage orifice (5) to the cup (2), the passage channel (6) having a cross-section which is constant or decreases towards the passage orifice (5) in a discharging direction of the flowable dental substance, and
    a closure cap (20) having a ring (23) resting against an outside wall of a side wall (4) of the cup (2) wherein a space exists between the ring (23) and an inner wall surface of the closure cap (20) when the closure cap (20) is attached to the dispensing device (1), wherein an entire exterior of said sidewall (4) of the cup (2) is in parallel alignment with an interior surface of said ring (23) and wherein said closure cap further comprises a protrusion that rests firmly against a bottom of said cup when said closure cap is attached to the dispensing device, and
    an application instrument (12), wherein the application instrument (12) is constructed in such a manner that at least a pick-up portion (13) thereof is insertable through the outlet orifice (3) into the cup (2) in order to pick up the flowable dental substance therein.

11. A dental-system with the storage/dispensing/application system according to claim 10, wherein the flowable dental substance (14) is provided in the container (10) and to be introduced into the cup (2) via the passage orifice (5) of the dispensing device (1).

12. The dental-system with a storage/dispensing/application system according to claim 10, wherein the flowable dental substance (14) is provided in the container (10) and to be introduced into the cup (2) via the passage orifice (5) of the dispensing device (1).

13. The storage/dispensing/application system according to claim 10, wherein the application instrument (12) is a microbrush.

14. The storage/dispensing/application system according to claim 10, wherein storage/dispensing system (9) further comprises a closure cap (20), the closure cap having
  a protrusion (22) projecting into the cup (2) of the dispensing device (1), and
  a ring (23) resting against the side wall (4) of the cup (2).

15. The storage/dispensing/application system according to claim 10, wherein the inside of the cup (2) has a volume of about 1 to about 30 mm$^3$.

16. The storage/dispensing/application system according to claim 10, wherein a circumferential collecting groove (7) is provided on the outside of the dispensing device (1) for collecting any flowable substance which escapes from the cup (2).

17. The storage/dispensing/application system according to claim 10, wherein the container (10) has an internal volume of about 1 about 20 ml.

18. The storage/dispensing/application system according to claim 10, wherein the storage/dispensing system (9) is opaque to at least a proportion of visible light.

19. The storage/dispensing/application system according to claim 10, wherein the passage orifice (5) has a cross-sectional area of about 0.001 to about 0.1 mm$^2$ and the outlet orifice (3) has a cross-sectional area of about 0.5 to about 5 mm$^2$.

20. The storage/dispensing/application system according to claim 10, wherein the inside of the cup (2) has a cross-section which is constant or reduces from the passage orifice (5) to the outlet orifice (3).

21. A method for the application of a flowable dental substance (14), comprising the following steps:
  providing a dental system with a storage/dispensing/application system, the storage/dispensing/application system including
    a storage/dispensing system (9) for the flowable dental substance, the storage/dispensing system including:
      a solvent-tight, resiliently deformable container (10) for the storage and provision of the flowable dental substance, and
      a dispensing device (1) connected to the container (10) for discharging the flowable dental substance from the container (10), the dispensing device having a cup (2) which has an outlet orifice (3) and a wall (4, 4') in which a passage orifice (5) is provided for introducing the flowable dental substance from the container (10), and a passage channel (6) on the opposite side of the passage orifice (5) to the cup (2), the passage channel (6) having a cross-section which is constant or decreases towards the passage orifice (5) in a discharging direction of the flowable dental substance, and
      a closure cap (20) having a ring (23) resting against an outside wall of a side wall (4) of the cup (2) wherein a space exists between the ring (23) and an inner wall surface of the closure cap (20) when the closure cap (20) is attached to the dispensing device (1), wherein an entire exterior of said sidewall (4) of the cup (2) is in parallel alignment with an interior surface of said ring (23) and wherein said closure cap further comprises a protrusion that rests firmly against a bottom of said cup when said closure cap is attached to the dispensing device, and
    an application instrument (12), wherein the application instrument (12) is constructed in such a manner that at least a pick-up portion (13) thereof is insertable through the outlet orifice (3) into the cup (2) in order to pick up the flowable dental substance therein,
  introducing the flowable dental substance into the cup (2) from the container (10) through the passage orifice (5),
  removing the flowable dental substance (14) from the cup (2) by means of the application instrument (12), and
  applying the flowable dental substance (14) by means of the application instrument (12).

22. A storage/dispensing system (9) for a flowable dental substance, comprising
  a solvent-tight, resiliently deformable container (10) for the storage and provision of the flowable dental substance, and a dispensing device (1) connected to the container (10) for discharging the flowable dental substance from the container (10), the dispensing device having a cup (2) which has an outlet orifice (3) and a wall (4, 4') in which a passage orifice (5) is provided for introducing the flowable dental substance from the container (10), and a passage channel (6) on the opposite side of the passage orifice (5) to the cup (2), the passage channel (6) having a cross-section which is constant or decreases towards the passage orifice (5) in a discharging direction of the flowable dental substance, and a closure cap (20) having a protrusion (22) projecting into the cup (2) of the dispensing device (1), and a ring (23) resting against a side wall (4) of the cup (2), wherein a circumferential collecting groove (7) is provided on the outside of the dispensing device (1) for collecting any flowable substance which escapes from the cup (2).

23. A storage/dispensing/application system for a flowable dental substance, comprising a storage/dispensing system (9) for flowable dental substance, including a solvent-tight, resiliently deformable container (10) for the storage and provision of the flowable dental substance, and a dispensing device (1) connected to the container (10) for discharging the flowable dental substance from the container (10), the dispensing device having a cup (2) which has an outlet orifice (3) and a wall (4, 4') in which a passage orifice (5) is provided for introducing the flowable dental substance from the container (10), and a passage channel (6) on the opposite side of the passage orifice (5) to the cup (2), the passage channel (6) having a cross-section which is constant or decreases towards the passage orifice (5) in a discharging direction of the flowable dental substance, and an application instrument (12), wherein the application instrument (12) is constructed in such a manner that at least a pick-up portion (13) thereof is insertable through the outlet orifice (3) into the cup (2) in order to pick up the flowable dental substance therein, wherein a circumferential collecting groove (7) is provided on the outside of the dispensing device (1) for collecting any flowable substance which escapes from the cup (2).

* * * * *